US008129105B2

(12) United States Patent
Zuckerman

(10) Patent No.: US 8,129,105 B2
(45) Date of Patent: Mar. 6, 2012

(54) METHOD AND APPARATUS FOR THE NON-INVASIVE MEASUREMENT OF TISSUE FUNCTION AND METABOLISM BY DETERMINATION OF STEADY-STATE FLUORESCENCE ANISOTROPY

(75) Inventor: Ralph Zuckerman, Philadelphia, PA (US)

(73) Assignee: Ralph Zuckerman, Philadelphia, PA (US)

( * ) Notice: Subject to any disclaimer, the term of this patent is extended or adjusted under 35 U.S.C. 154(b) by 784 days.

(21) Appl. No.: 11/624,820

(22) Filed: Jan. 19, 2007

(65) Prior Publication Data

US 2007/0243521 A1 Oct. 18, 2007

Related U.S. Application Data

(60) Provisional application No. 60/744,831, filed on Apr. 13, 2006.

(51) Int. Cl.
*C12Q 1/00* (2006.01)
(52) U.S. Cl. ............................................. 435/4; 600/317
(58) Field of Classification Search ........................ None
See application file for complete search history.

(56) References Cited

U.S. PATENT DOCUMENTS

| | | | |
|---|---|---|---|
| 4,115,699 A | 9/1978 | Mizuta et al. | |
| 4,476,870 A | 10/1984 | Peterson et al. | |
| 4,579,430 A | 4/1986 | Bille | |
| 4,810,655 A | 3/1989 | Khalil et al. | |
| 4,947,850 A | 8/1990 | Vanderkooi et al. | |
| 5,039,219 A | 8/1991 | James et al. | |
| 5,120,510 A | 6/1992 | Gourley et al. | |
| 5,186,173 A | 2/1993 | Zuckerman | |
| 5,251,633 A | 10/1993 | Wunderling et al. | |
| 5,281,825 A | 1/1994 | Berndt et al. | |
| 5,317,162 A | 5/1994 | Pinsky et al. | |
| 5,318,023 A | 6/1994 | Vari et al. | |
| 5,341,805 A | 8/1994 | Stavridi et al. | |
| 5,383,452 A | 1/1995 | Buchert | |
| 5,495,850 A | 3/1996 | Zuckerman | |
| 5,515,864 A | 5/1996 | Zuckerman | |
| 5,626,134 A | 5/1997 | Zuckerman | |
| 5,701,902 A | 12/1997 | Vari et al. | |
| 6,007,994 A * | 12/1999 | Ward et al. ........................ | 435/6 |
| 2004/0021848 A1 | 2/2004 | Bambot et al. | |
| 2005/0080323 A1 | 4/2005 | Kato | |

FOREIGN PATENT DOCUMENTS

WO WO2005/032361 4/2005

OTHER PUBLICATIONS

Mohanty S.K. et al. Depolarization of autofluorescence from malignant and normal human breast tissues, Applied Optics, Mar. 2001, vol. 40, No. 1, pp. 1147-1154.*
Vishwasrao H.D. et al. Conformational dependence of intracellular NADH on metabolic state revealed by Associated fluorescence anisotropy, The Journal of Biological Chemistry, (Published, JBC papers in press, Apr. 29, 2005), Jul. 2005, vol. 280, No. 26, pp. 25119-25126.*
Elson D. et al. Biomedical applications of fluorescence lifetime imaging, Optics& Photonics News, Nov. 2002, pp. 27-32 and 56-57.*
Zuckerman R. et al. Noninvasive measurement of mitochondrial function in space, time and depth in retinal tissue: Metabolic mapping, Invest. Ophthalmol. Vis. Sci., 2005, vol. 46, No. 5, Suppl. S, p. 4759; ARVO Meeting Abstracts, May 1st to 5th, 2005, Ft. Lauderdale, Fl. USA.*
U2: Schweitzer D. et al. Evaluation of time-resolved autofluorescence images of the ocular fundus, Proc. of SPIE-OSA Biomedical Optics, (Online publication date, Oct. 29, 2003), Proc. SPIE 2003, vol. 5141, pp. 8-17.*
Huang S. et al. Two-photon fluorescence spectroscopy and microscopy of NAD(P)H and flavoprotein, Biophysical Journal, May 2002, vol. 82, pp. 2811-2825.*
Foster Lab Web Publication at—http://www.urmc.rochester.edu/smd/rad/foster/research/fluorescenceanisotropy/index.html; Fluorescence anisotropy: Confocal fluorescence polarization microscopy, Sep. 20, 2003, pp. 1-2.*
Kostov Y. et al. Polarization oxygen sensor: a template for a class of fluorescence-based sensors, Anal. Chem., May 1, 2002, vol. 74, No. 9, pp. 2167-2171.*
D. Schweitzer et al., "Veränderungen der Autofluoreszenzlebensdauer am Fundus nach Sauerstoffprovokation", Ophthalmologe 2004, 101:66-72 (2003).
International Searching Authority for WIPO, "International Search Report and Written Opinion for PCT/US/2007/063768", Mar. 12, 2007.
L. Sacconi et al., Overcoming photodamage in second-harmonic generation microscopy: Real-time optical recording of neuronal action potentials, PNAS, Feb. 28, 2006, pp. 3124-3129, vol. 103, No. 9.
Vanderkooi, J. et. al., "An Optical Method for Measurement of Dioxygen Concentration Based Upon Quenching of Phosphorescence", J. Biol., Chem., 262(12); 5476-5482 (Apr. 1987).
Wangsa-Wirawan, et al., "Retinal Oxygen: Fundamental and Clinical Aspects," Arch. Ophthalmol., 121: 547-557. (2003).
de Coo, F. A., Zonnenberg, B. A., and Trap, N. H., "Prolonged Normothermic Perfusion of the Isolated Bovine Eye: Initial Results", Curr Eye Res., 12(4): 293-301 (Apr. 1993).
Yu et al., "Intraretinal oxygen distribution in the monkey retina in response to systemic hyperoxia," Invest Ophthalmol Vis Sc, 46, 4728-4733. (2005).
Zuckerman et al., "Optical mapping of inner retinal tissue PO2 "Current Eye Res, 12, 809-825 (1993).

* cited by examiner

*Primary Examiner* — Jon P Weber
*Assistant Examiner* — Satyendra Singh
(74) *Attorney, Agent, or Firm* — Knobbe Martens Olson & Bear LLP

(57) ABSTRACT

A non-invasive measurement of biological tissue reveals information about the function of that tissue. Polarized light is directed onto the tissue, stimulating the emission of fluorescence, due to one or more endogenous fluorophors in the tissue. Fluorescence anisotropy is then calculated. Such measurements of fluorescence anisotropy are then used to assess the functional status of the tissue, and to identify the existence and severity of disease states. Such assessment can be made by comparing a fluorescence anisotropy profile with a known profile of a control.

12 Claims, 9 Drawing Sheets

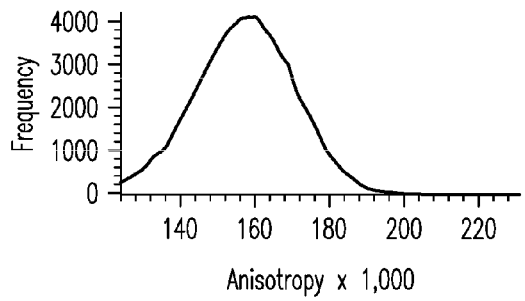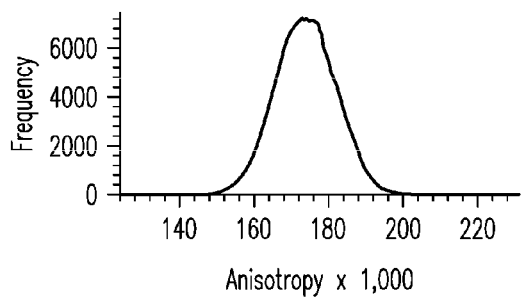
FIG.4A  FIG.4B
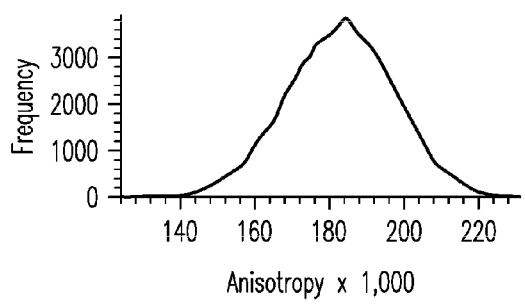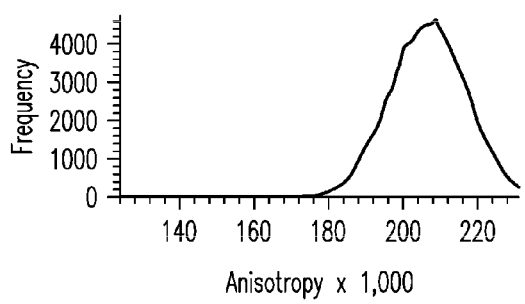
FIG.4C  FIG.4D
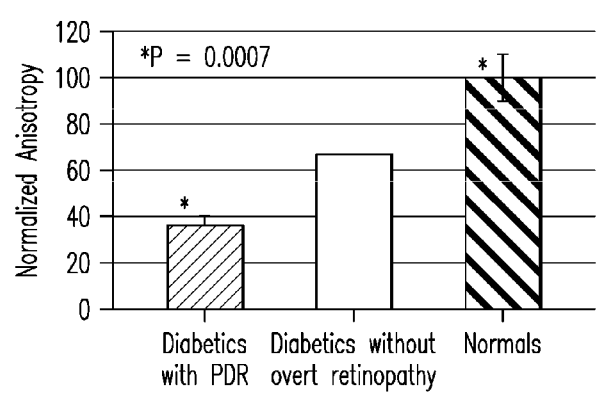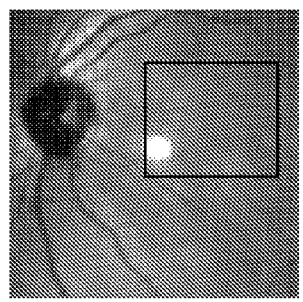
FIG.4E  FIG.4F

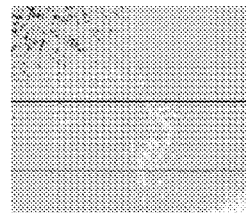
FIG.5A    FIG.5B
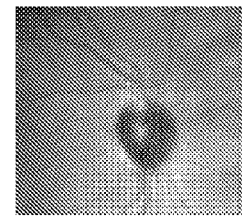
FIG.5C    FIG.5D
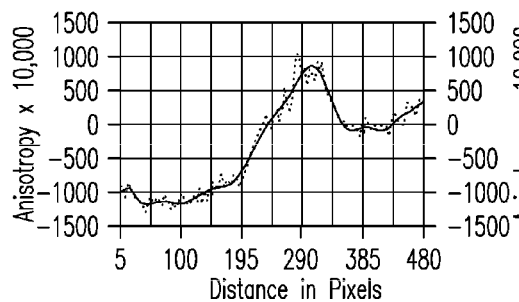
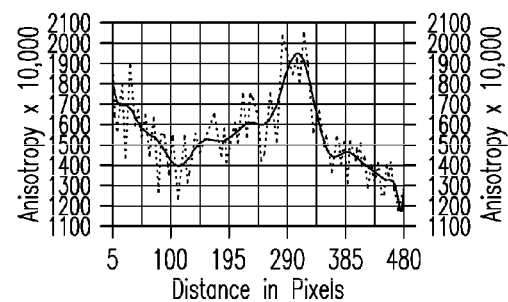
FIG.5E    FIG.5F
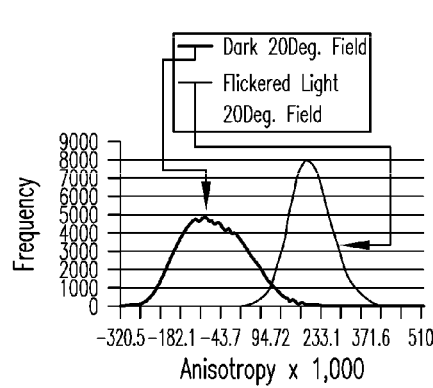
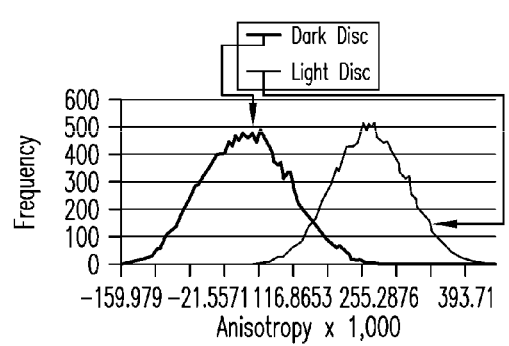
FIG.5G    FIG.5H

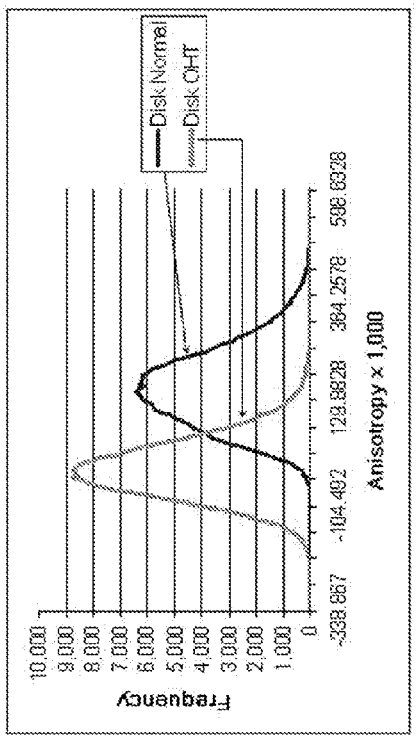
FIG.7B
FIG.7C
FIG.7A
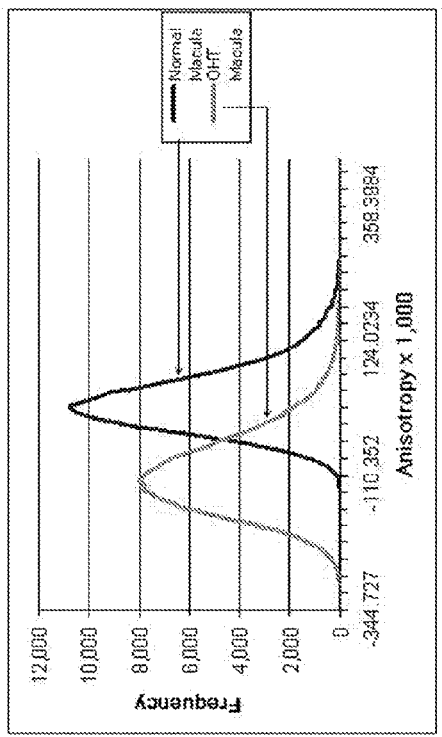
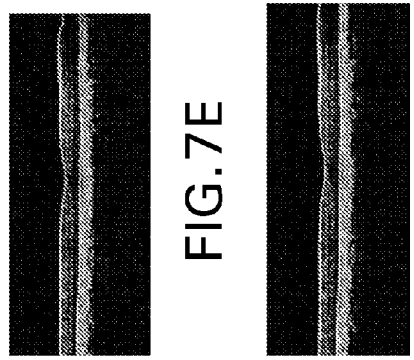
FIG.7E
FIG.7F
FIG.7D

METHOD AND APPARATUS FOR THE NON-INVASIVE MEASUREMENT OF TISSUE FUNCTION AND METABOLISM BY DETERMINATION OF STEADY-STATE FLUORESCENCE ANISOTROPY

CROSS-REFERENCE TO PRIOR APPLICATION

Priority is claimed from U.S. Provisional Patent Application Ser. No. 60/744,831, filed Apr. 13, 2006, the entire disclosure of which is incorporated by reference herein.

BACKGROUND OF THE INVENTION

This invention relates to the field of non-invasive measurements of functions of biological tissues.

Structural damage in living tissues is always accompanied by functional deficit. However, the converse is not necessarily true. That is, functional deficit may precede irreversible structural damage for many years, in numerous disease states, and may therefore serve as a diagnostic indicator of early disease and a prognostic indicator of disease progression. For this reason, increasing attention has focused on functional imaging of tissues, in situ, in humans.

PET scanning provides striking images of functional change; however, its resolution is crude and its implementation expensive.

To provide high-resolution imaging of the functional state or metabolic rates of tissues non-invasively and in situ, optical techniques must be employed. The present invention provides such an optical technique.

The functional status of bodily tissues is stoichiometrically related to tissue metabolism through the well-established mechanism of respiratory control. In particular, in the process of electron transfer from substrates such as glucose and pyruvate to molecular oxygen, the oxidation of the flavin adenine dinucleotide $FADH_2$ to FAD produces 2 molecules of adenosine triphosphate (ATP), while the oxidation of the nicotinamide adenine dinucleotide NADH to NAD yields 3 ATPs. ATP in turn is used to power processes within living cells that support function within all living cells. Therefore, the conversions of these two nucleotides may be used to monitor cellular function and serve as sensitive indicators of cellular and tissue health.

Both flavin and nicotinamide dinucleotides possess fluorescence properties and lifetimes that change with cellular function and both are endogenous fluorophors that are found within mitochondria as well as in enzymes within other cellular compartments in tissues. Prior measurements of the fluorescence intensity of either or both, or of the ratio of fluorescence intensities of these molecules, have been used in research studies by Chance and his colleagues to explore metabolism in a research setting. However, these approaches have never successfully been extended to the clinical setting because they require calibration of the system by bringing the tissue to a uniform oxygen partial pressure of 0 mm Hg by breathing an animal on 100% nitrogen. This obviously cannot be done in humans without causing irreversible cell death.

The need to calibrate fluorescence intensity measurements arises from the photobleaching of fluorophors during exposure to excitation light. Moreover, fluorescence intensity is influenced by other factors that have no relation to metabolism, such as absorption of excitation and emission light by intervening tissues. To overcome these deficiencies, some have tried to take the ratio of emissions from NADH and FAD, but the results have not been satisfactory because the rates of photobleaching of these molecules are different, thus precluding a clinically useful tool.

In theory, the problems associated with fluorescence intensity measurements may be overcome by measuring fluorescence lifetime, namely the decay constant of fluorescence emission following pulse excitation. However, the fluorescence lifetimes of interest would require the use of femtosecond laser pulses. Even with the use of photon counting photomultipliers, such a technique would require, for adequate signal-to-noise ratio, an excitation energy that would destroy tissue.

U.S. Pat. No. 5,626,134, the disclosure of which is incorporated by reference herein, describes a novel procedure for the steady-state measurement of fluorescence lifetime, based upon the measurement of fluorescence anisotropy. The disclosed general methodology overcomes the deficiencies of time-resolved measurements of fluorescence lifetime in both in vivo and in vitro applications.

The present invention provides a modified technique which can be applied to the non-invasive measurement of the steady-state fluorescence anisotropies of flavin and nicotinamide dinucleotides within bodily tissues. As will be shown in detail below, the present invention uses measurements of steady-state fluorescence anisotropy to reveal tissue functional and metabolic status, and changes in function and metabolism that accompany disease states. Moreover, and of singular importance, steady-state fluorescence anisotropy is employed in the present invention to reveal numerous aspects of metabolically-induced changes in these endogenous nucleotides, namely, fluorescence lifetime changes that occur during function and metabolic change as well as conformational changes and changes from the unbound to bound form of these nucleotides that also take place during metabolism and function within bodily tissues.

In the present invention, the application of steady-state fluorescence anisotropy measurement is a more encompassing and broader methodology for probing the functional and metabolic state of a bodily tissue in situ by non-invasive methods in health and disease. The method and apparatus thereby provide the first safe, sensitive, calibration-free optical methodology for the non-invasive measurement of metabolic rate and functional status of tissues in 2- and 3-dimensional space.

Ideally, a noninvasive optical approach that reveals function by imaging metabolic changes should yield signals that are quantitatively traceable to function based upon the stoichiometric relationship between function and metabolism that is imposed by respiratory control. Redox fluorometry is one well-established approach that fulfills this criterion. For this reason, redox fluorometry employing the intrinsic fluorescence of reduced pyridine nucleotides and oxidized flavoproteins has long been employed to assess cellular energy metabolism. However, such intensity-based methods are severely limited due to photobleaching, inner filter effects and the difficulties associated with isolating contributions from these metabolically relevant fluorophores from the background autofluorescence of other endogenous fluorophores. Inner filter effects are present in all tissues. Although measurements of fluorescence lifetime can, to some extent, overcome the limitations of intensity-based measurements, the information gleaned from such measurements alone is limited, and ultra fast lifetimes require the use of high energy laser pulses that may be damaging to fragile tissues.

The present invention includes a novel method of steady-state flavoprotein fluorescence anisotropy imaging (metabolic mapping) that overcomes the deficiencies of intensity- or lifetime-based imaging while retaining the essential quantitative coupling of metabolism to function. The steady-state fluorescence anisotropy (A) of a distinct molecular species undergoing isotropic rotational diffusion is related to the excited state lifetime τ and the rotational correlation time φ by the following equation:

$$\frac{A_o}{\overline{A}} = 1 + \frac{\tau}{\phi} = 1 + \sigma \quad (1)$$

where $A_o$ is a limiting value (in the absence of rotation) given by the relative orientation of the absorption and emission dipole transition moments, and σ is the ratio τ/φ.

From this equation it follows that fluorescence anisotropy is a parameter with the capability of revealing changes in both orientation distribution and excited state lifetimes with great sensitivity. Such function-induced metabolic changes could arise from restrictions to diffusional motion, complex formation and molecular proximity manifested by hetero- or homo-energy transfer. Moreover, fluorescence anisotropy and lifetime are intrinsic parameters, unlike the intensity signals used to compute them, and are therefore insensitive to light path and geometry. When measurements are restricted to a single intrinsic fluorophore, the effects of photobleaching are also eliminated. All of these advantages contribute to the capability of making reliable comparisons over time in the same tissue in situ and between different living tissues.

Fluorescence anisotropy is independent of fluorophore concentration, and therefore, unlike fluorescence intensity-based imaging or structural technologies, its sensitivity is independent of the thickness of the tissue being probed. Of especial importance is the large safety margin of the method of the present invention that allows it to be employed to probe cellular bioenergetics in living tissues in humans and the ability to bandpass and notch filter anisotropy values provides the opportunity to reject contributions from other endogenous fluorophores.

Flavoprotein (FP) fluorescence can be excited by longer wavelength, lower energy light, is more resistant to photobleaching than pyridine nucleotides (NADH or NADPH) and is almost singularly associated with mitochondria (Koke et al, "Sensitivity of flavoprotein fluorescence to oxidative state in single isolated heart cells", Cytobios (1981), vol. 32, p. 139-145; Scholz et al, "Flavin and pyridine nucleotide oxidation-reduction changes in perfused rat liver", J. Biol. Chem. (1969), vol. 244, p. 2317-2324). By restricting measurements to FP steady-state fluorescence anisotropy, the risk of damage to tissues by high energy laser pulses is obviated by the use of lower energy light distributed over durations that are long relative to the excited state lifetimes. Of the numerous enzymes endowed with flavin cofactors, it has been previously shown that lipoamide dehydrogenase (LipDH) dominates the fluorescence signal with lesser contributions from electron transfer flavoprotein (ETF). LipDH serves as a direct probe of cellular metabolism and function because its FAD cofactor is in direct equilibrium with the mitochondrial NAD+/NADH pool, while the redox state of ETF is indirectly affected by the NAD+/NADH ratio within mitochondria.

It should also be noted that time-resolved fluorescence anisotropy measurement requires the use of ultra-fast laser pulses that would similarly be destructive to tissues. For this reason, steady-state fluorescence anisotropy determination is employed in the current invention. Furthermore the measurement of flavin dinucleotide fluorescence anisotropy is a preferred embodiment of the technology because longer excitation wavelengths and thus lower excitation energies may be employed, thereby ensuring the safety of its use in delicate tissues such as in the non-invasive imaging of the functional status of the human retina, in situ, in the eye.

Although, the methodology disclosed herein is directed toward non-invasive measurement of the fluorescence anisotropies of flavin and nicotinamide dinucleotides, and thereby the metabolic and functional status of tissues, it will be apparent to one skilled in the art that this is a general methodology that may be applied to all endogenous fluorophors whose steady-state fluorescence anisotropies may be influenced by disease processes.

The present invention also includes a method for extending the sensitivity of the above-described non-invasive method by measuring the steady-state fluorescence anisotropy of the tissue first in the resting state and subsequently in the stimulated state. Steady-state fluorescence anisotropy maps are acquired in these two states in 2- or 3-dimensional space and the anisotropy map in the resting state is subtracted point-by-point from that obtained in the stimulated state. The resultant fluorescence anisotropy map therefore reveals the capacity of the tissue to respond to stimulation. As such, the methodology has clear application to detection and prognosis of disease states wherein the magnitude of change to stimulation may be reduced and the spatial loci of functional and metabolic deficits identified.

SUMMARY OF THE INVENTION

The present invention provides apparatus and methods for the non-invasive determination of the functional and metabolic status of tissues by the measurement of the steady-state fluorescence anisotropies of one or more endogenous fluorophors, in situ, such as flavin and nicotinamide dinucleotides. By use of the present invention, the rotational and vibrational motions of the isoalloxazine ring of FAD have been exploited to extract, by relatively simple means, a measurement of fluorescence lifetime, thereby providing the first safe, high-resolution, calibration-free measurement of metabolic rate and function in tissues. In addition, steady-state fluorescence anisotropy can reveal conformational or binding changes in endogenous fluorophors such as FAD and NADH that accompany changes in cellular and tissue metabolism.

The non-invasive measurement of functional and metabolic state of bodily tissues is accomplished by irradiating the tissue with continuous polarized excitation light, characterizing the polarization properties of the emitted fluorescence from endogenous fluorophors in a manner that provides information sufficient to calculate steady-state fluorescence anisotropy, and employing the calculated fluorescence anisotropy values to describe tissue metabolism and functional activity of the tissue.

Fluorescence anisotropy may be measured at a plurality of points in space, thereby providing a topographic measurement of the functional and metabolic state of the tissue. Similarly, optical serial sectioning techniques may be employed non-invasively to provide spatial maps of functional and metabolic states of tissues, at various depths within the tissue. Consequently, the present invention provides a sensitive, calibration-free, high-resolution methodology for the non-invasive measurement of the functional and metabolic state of bodily tissues in space, time and depth.

The invention also includes a novel method of filtering the range of fluorescence anisotropy values to isolate steady-state fluorescence anisotropy measurements to a specific endogenous fluorophor.

The invention also includes an apparatus and method for measuring steady-state fluorescence anisotropy tomographically, in 3-dimensional space, and in which the apparatus is coupled to a confocal scanning system.

The present invention also includes means for extending the sensitivity of the above-described method in disease detection. By first measuring steady-state fluorescence anisotropy in the resting state, and then performing the same measurement in the stimulated state, at a plurality of points in space, and subtracting the measurements in the resting state from those in the stimulated state, one can detect disease-induced reductions in the magnitude of change to stimulation, and can localize these disease-induced deficits in 2- and 3-dimensional space.

The present invention therefore has the primary object of providing an apparatus and method for the noninvasive determination of the metabolic and functional status of biologic tissues, in situ, by measurement of steady-state fluorescence anisotropies of flavin adenine and nicotinamide adenine dinucleotides.

The invention has the further object of providing an apparatus and method for the non-invasive determination of the metabolic and functional status of biologic tissues in situ topographically, in 2-dimensional space, and tomographically in 3-dimensional space.

The invention has the further object of enabling non-invasive early detection of disease by measuring the effects of the disease on the functional and metabolic state of tissues.

The invention has the further object of enabling prognosis of disease progression by virtue of the change in functional and metabolic state of tissues over time, in the same patient, and the comparison of a patient's changing metabolic profiles to a normative database of disease progression established in clinical trials.

The invention has the further object of enabling detection of disease prior to irreversible structural damage, by measurement of functional and metabolic changes that precede such irreversible structural damage.

The invention has the further object of guiding therapeutic interventions that are directed toward ameliorating disease, by non-invasive and non-destructive monitoring of the effects of therapeutic interventions on the metabolic and functional status of tissues.

The invention has the further object of determining the specific locations of disease-induced deficits in tissue function, by measuring such tissue in a resting state and in a stimulated state, and by comparing such measurements precisely at various points in a two- or three-dimensional space.

The reader skilled in the art will recognize other objects and advantages of the invention, from a reading of the following brief description of the drawings, the detailed description of the invention, and the appended claims.

BRIEF DESCRIPTION OF THE DRAWINGS

FIGS. 4A-4F provide diagrams illustrating the use of the present invention to detect diabetic retinopathy, where FIGS. 4A-4D provide frequency histograms showing the variation in fluorescence anisotropy under various conditions, FIG. 4E provides a graph summarizing the results, and FIG. 4F provides a scan of the retina showing the area of interest.

FIGS. 5A-5H illustrate the use of the present invention to analyze tissue function by comparing fluorescence anisotropy maps taken in a resting state and in a stimulated state, wherein FIGS. 5A-5C depict a portion of the retina in resting and stimulated conditions and showing a comparison of the two states, FIG. 5D provides a scan of the region of interest, and FIGS. 5E-5H provide graphs analyzing the results.

FIGS. 7A-7F illustrate the use of the present invention in detecting ocular hypertension, where FIGS. 7A and 7D provide frequency histograms of fluorescence anisotropy for various conditions, and FIGS. 7B, 7C, 7E, and 7F provide tomographs showing the eye under various conditions.

DETAILED DESCRIPTION OF THE INVENTION

Figure 1:
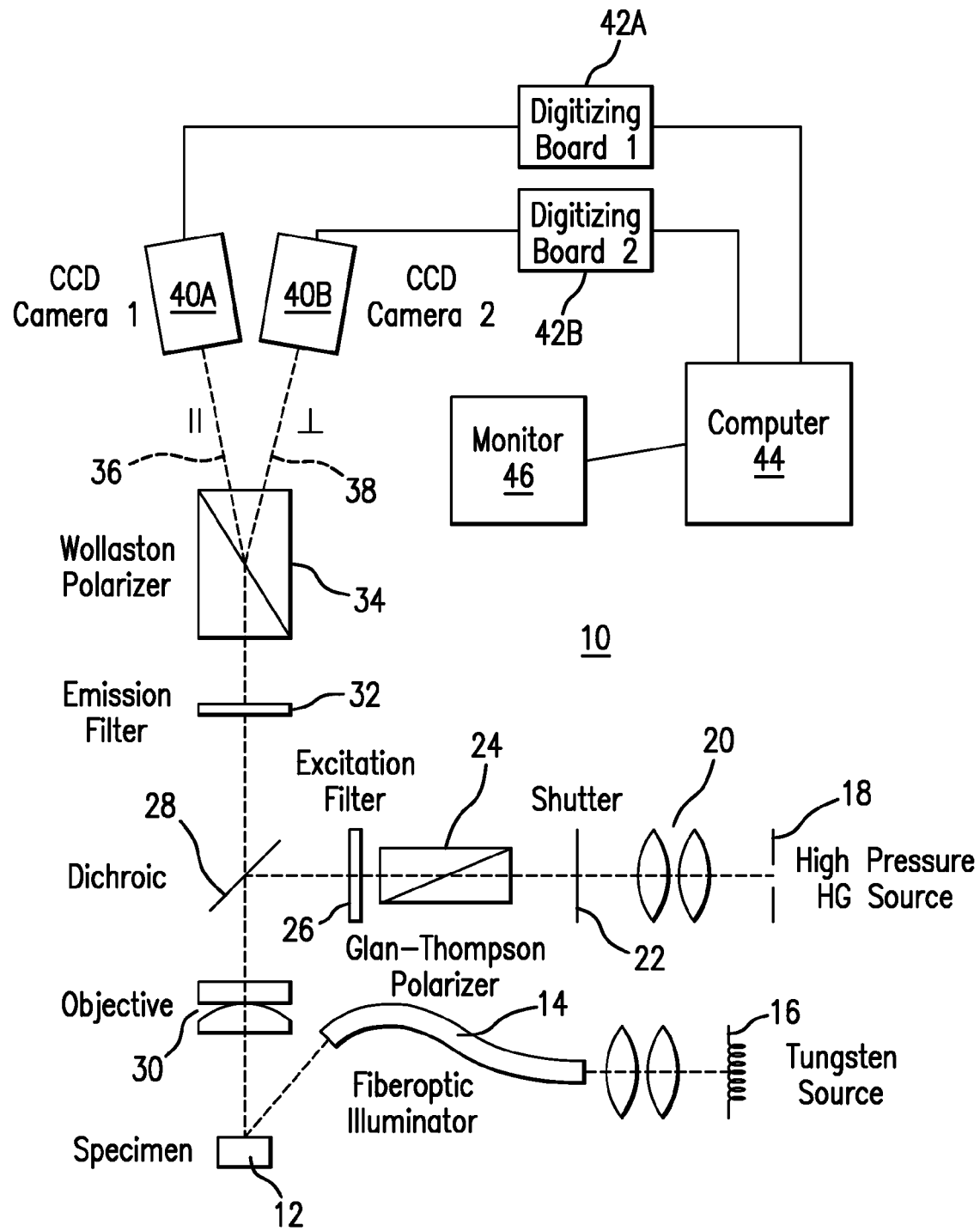
FIG. 1 provides a schematic diagram of an imaging apparatus used to measure tissue function and metabolism, according to the present invention.

FIG. 1 provides a schematic diagram of an apparatus 10 designed for the topographic, 2-dimensional, mapping of tissue function and metabolism non-invasively in an imaged tissue. Specimen 12 includes one or more biological tissues which contain one or more substances, called fluorophors, which fluoresce when illuminated.

Specimen 12 is illuminated with nonpolarized visible light by a fiberoptic illuminator 14 utilizing a tungsten source 16. The radiant energy of a xenon arc lamp 18 is gathered by a collector lens 20, and is selectively allowed to pass through shutter 22. The light then passes through a Glan-Thompson polarizer 24 (obtained from Ealing, Inc.).

The light is spectrally shaped by an excitation filter 26 and is then reflected by a dichroic mirror 28 (obtained from Omega Optical) which reflects excitation wavelengths through an objective lens 30 to the imaged tissue, causing fluorophors in the tissue to fluoresce.

Emitted luminescence from the excited tissue 12 is gathered by the objective lens 30 and passes through the dichroic mirror 28, and through an emission filter 32, which passes emission wavelengths to a Wollaston prism polarizer 34 which resolves the emitted fluorescence into its linearly polarized components parallel 36 and perpendicular 38 to the plane of excitation polarization. The parallel and perpendicular vector components 36, 38 are respectively and simultaneously detected by the CCD (charge coupled devices) chips of two video cameras 40A and 40B (e.g. Xybion model 250).

Alternative optical detectors with sufficient spatial resolution, such as slow scan chilled CCD cameras, SIT or ISIT tube cameras, or photodiode arrays (not shown), would also be suitable for the detection of the two-dimensional distributions of the parallel and perpendicular components of the emitted fluorescence.

The outputs of the two video cameras are digitized by two digitizing boards 42A and 42B (such as sold by Imaging Technologies or under the designation model DT3851 by Data Translation) within a microcomputer 44, (e.g., an IBM or equivalent computer, preferably having a processing chip operating at 33 or 66 MHz). Such a device is sufficient for the task and for subsequent image processing prior to display on the monitor 46.

Figure 2:
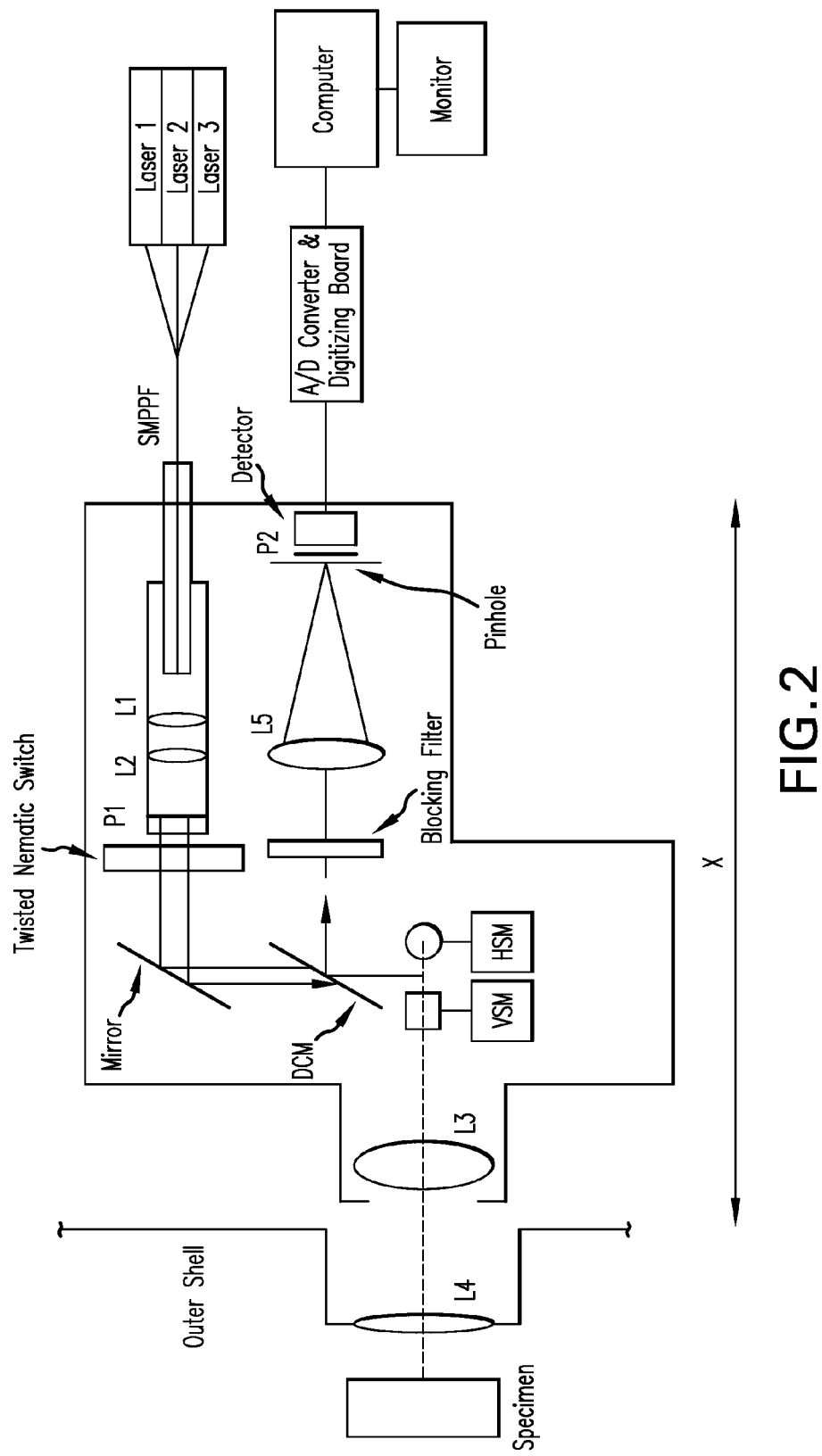
FIG. 2 provides a schematic diagram of an imaging apparatus, made according to the present invention, for deriving three-dimensional maps of tissues.

FIG. 2 provides a schematic of an apparatus designed for the tomographic (3-dimensional) mapping of tissue metabolism and function, according to the present invention. Light from one tunable argon laser (e.g. Melles Griot part number 35 LAP 321-240) and two diode lasers (e.g. Melles Griot part number 56 ICS 008-HS) input light into the confocal device by means of a trifurcated single mode polarization fiber (such as sold by Ealing Inc. under the designation of catalog number 34-5223), denoted in FIG. 2 as SMPPF.

The excitation or imaging wavelength is selected by computer-controlled selection of the appropriate laser, and in the case of the argon laser by tuning the laser and by the additional use of computer-selectable narrow bandpass filters. The argon laser permits excitation at 488 nm for fluorescence anisotropy measurements from FAD, as well as 514 nm for observing the tissue in reflection mode. The diode lasers permit observation of the tissue at 730 nm or 830 nm in reflection mode. Other light sources emitting light at other wavelengths may be employed in this embodiment.

The small diameter fiber (<150 μm) serves as a point source that is collimated by a lens system (L1 and L2). The collimated light passes through a linear polarizer P1 (which may be obtained from Meadowlark Optics, part number C001298) and then passes through a custom fabricated LCD twisted nematic switch (such as Meadowlark Optics part no. C001700). The twisted nematic switch allows rapid rotation of the plane of polarization of the collimated light incident on it by 90° with rise times of the order of 20 msec. The linearly polarized light at either orthogonal plane of polarization is reflected by a front surface mirror and the collimated polarized light passes through a dichroic mirror, designated DCM in FIG. 2 (such as can be obtained from Chroma or Omega Optics) to fall incident on two servo-controlled mirrors VSM and HSM that serve as a scanning system.

Movement of the mirrors VSM and HSM causes light to scan a tissue sample in a raster fashion, in vertical and horizontal directions, respectively, thereby performing a two dimensional scan of the tissue.

The light for either fluorescence excitation, or imaging in reflection mode, at any of three wavelengths, passes through the first component of the objective, lens L3, and subsequently through the second component of the objective, housed in the outer shell, L4. Fluorescence emission or reflected light from the tissue returns through objective lenses L4 and L3 and is scanned by mirrors VSM and HSM onto the dichroic mirror DCM. The dichroic mirror DCM reflects light at wavelengths >500 nm, and this light, in turn, passes through a longpass interference filter (such as Chroma part number HQ5101p) that transmits light >500 nm and rejects light <500 nm by 5 orders of magnitude (O.D. >5 from 300-500 nm).

Light of wavelengths >500 nm is imaged onto a pinhole by L5 and then passes through a linear polarizer P2 (which may be Meadowlark Optics, part number C001298) with its plane of polarization set parallel to that of P1. Light passing through P2 falls onto the detector surface of a custom-made high-sensitivity photomultiplier module (such as Hamamatsu part number H9656-20MOD W/2.5 MHz AMP), depicted as a "detector" in FIG. 2. The output of the photomultiplier module is digitized and bitmap images of 512×512 pixels are saved in random-access memory (RAM) and stored to disk. Other detectors such as avalanche photodiodes may replace the photomultiplier. The resolution of the scanning may be adjusted to any desired resolution by selection of alternative scanning systems and servo controllers.

For fluorescence anisotropy imaging, rotation of the plane of polarization by the twisted nematic switch is synchronized with the full frame acquisition speed, thereby exciting the tissue at orthogonal planes of polarization in succession. In the embodiment shown, the scan time for a full frame is 28 msec. By actuating the twisted nematic, fluorescence emission is resolved into vector components parallel and perpendicular to the plane of polarization of P2, thus providing vector components $I_\parallel$ and $I_\perp$ employed in the calculation of fluorescence anisotropy, according to the following equation:

$$A = \frac{I_\parallel - GI_\perp}{I_\parallel + 2GI_\perp}$$

where G is an empirical correction factor used to correct for transmission efficiency in parallel and perpendicular planes.

The system is automated and synchronized to acquire sequential fluorescence emission images in parallel and perpendicular planes at speeds ranging from 6 to 25 Hz. Any desired number of frames corresponding to orthogonal planes of polarization may be acquired and averaged to eliminate shot noise, and the images in the case of tissues that are moving, such as in the eye, are aligned by software for translational and rotational movements.

The tissue is brought into focus by moving the outer shell with the inner assembly fixed in position. The entire inner assembly of the confocal metabolic mapper is motorized for translation in the x direction as depicted and the inner assembly may be moved in selectable discrete steps by a stepping motor.

Sectioning the tissue at desired resolution within the depth of the tissue for both fluorescence anisotropy maps and reflection images is performed by appropriate selection of the size of the pinhole and the size of the displacement of the inner assembly by the stepping motor. In this manner, tomographic fluorescence anisotropy maps in 3-dimensional space may be acquired. Similarly for fluorescence anisotropy mapping of other endogenous fluorophors such as NADH, alternative pairs of DCM and blocking filters may be switched in by computer-actuated linear solenoids.

To implement a system that has appropriate sensitivity to metabolic and functional changes in the examined tissue, it becomes necessary to restrict steady-state anisotropy to the relevant fluorophor that provides such information, e.g., FAD. In other words, all tissues contain a number of endogenous substances that fluoresce at a given excitation wavelength, and it becomes necessary to extract information from the metabolically-relevant fluorophor from the total background fluorescence arising from multiple fluorophors within the tissue.

In principle, one can extract information from the fluorophor of interest by spectrally shaping excitation and emission filters. However, this procedure is rarely sufficient to accomplish this important task. For this reason, the present invention provides a new approach, described below, that deals with the range of steady-state fluorescence anisotropy values calculated from fluorescence emissions.

To develop a means for isolating fluorescence anisotropy to a given fluorophor, the tissue can be imaged using the optical device shown in FIG. 1, wherein the CCD detectors for parallel and perpendicular vector components are replaced by fiber optic coupled high sensitivity grating spectrometers (e.g. Ocean Optics, part number USB4000-VIS-NIR) that average over the full field of view. In this manner, fluorescence anisotropy arising from the tissue can be determined as a function of wavelength. Using the formula given above (and in the aforementioned U.S. Pat. No. 5,626,134), one can produce software which will calculate fluorescence anisotropy from vector components of fluorescence emission parallel and perpendicular to the plane of polarization of the excitation light, and to display fluorescence anisotropy as a function of emission wavelength.

By appropriate spectral shaping of the incident excitation light and bandpass filtering, i.e., limiting the range of collected anisotropy values, the emission anisotropy spectrum can be constrained closely to match published values of the fluorescence emission spectrum of known fluorophors, such as FAD or NADH. The same procedure can be applied to isolate contributions from other endogenous fluorophors, the changes in fluorescence anisotropy of which may be relevant to other disease conditions. The results of such a procedure are summarized in FIG. 9, discussed below.

Figure 9:
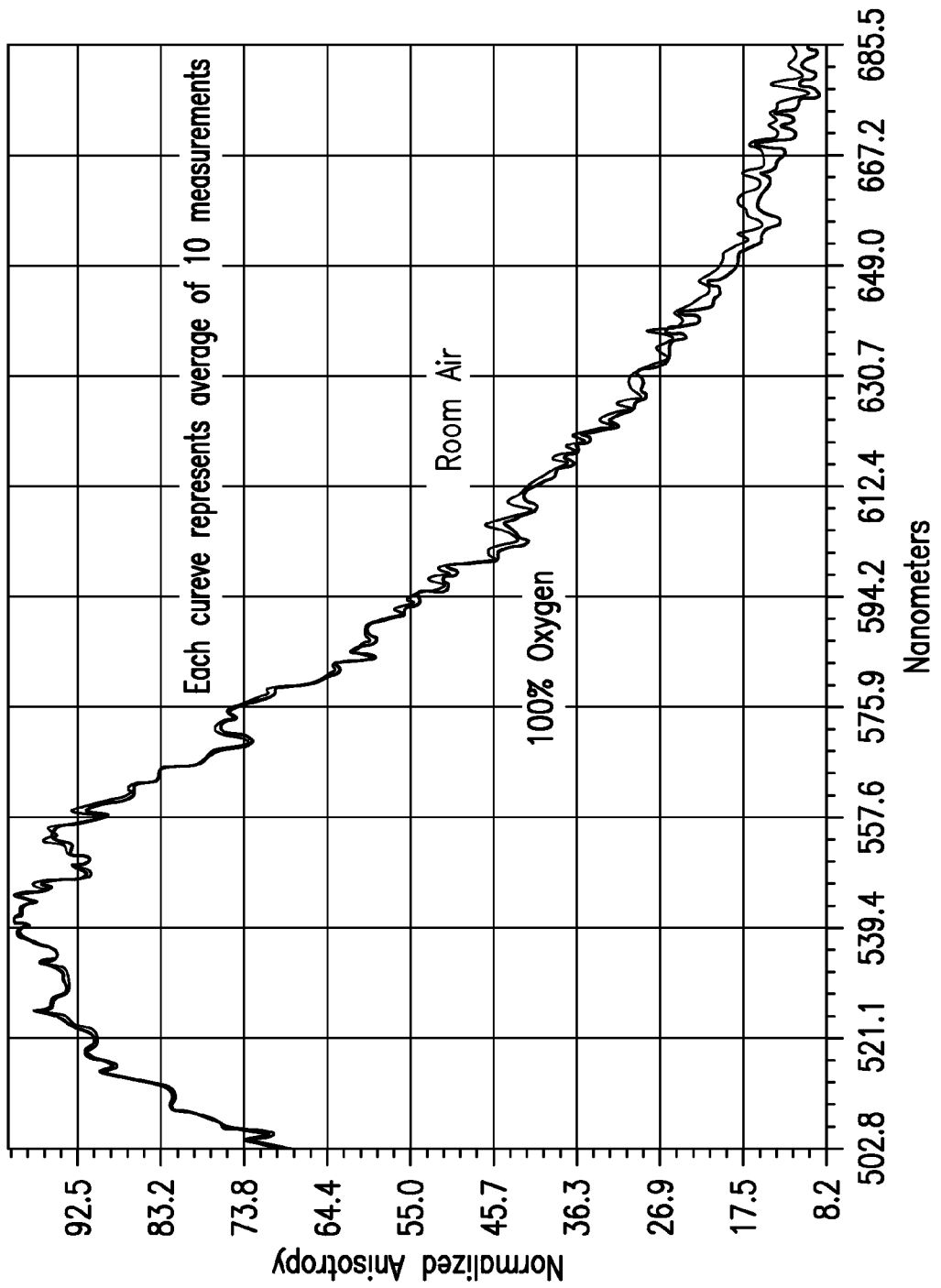
FIG. 9 provides a graph showing fluorescence anisotropy values generated from measurements of a human retina, according to the present invention, the figure showing a curve based on measurements taken while a subject is breathing pure oxygen, and a curve based on measurements taken while the subject is breathing pure air.

To test the ability of the above-described procedure to isolate steady-state fluorescence anisotropy due to FAD only, a human retina was imaged with 488 nm excitation light and the fluorescence anisotropy calculated from the emitted fluorescence vector components determined as a function of wavelength. The measurements were performed with the subject breathing either room air or 100% oxygen. Fluorescence anisotropy values were bandpass filtered until fluorescence anisotropy plotted as a function of wavelength closely matched the fluorescence emission spectrum of FAD as found in the literature. Since fluorescence anisotropy changes in magnitude when the subject breathes oxygen, as compared to room air, it is possible to test the efficacy of this novel procedure by normalizing the results obtained under room air and 100% oxygen conditions. If the procedure of the present invention is effective, then the two graphs should overlap when normalized. This is precisely what is obtained in practice. FIG. 9 provides a graph showing curves representing the two conditions of measurement.

In summary, the present invention enables the user to fit an anisotropy profile to a profile of a known fluorophor, by appropriate adjustment of filter parameters. Such adjustment would preferably, but not necessarily, be done entirely by software. Then, a device made according to the present invention could be directed at an unknown sample, with the parameters set as previously determined, and one would know, with confidence, that the results obtained were due to the particular substance of interest.

More specifically, in the example discussed above, in which the fluorophor of interest is FAD, one would select the parameters so that the anisotropy diagram fits the known profile for FAD, meaning that the system has isolated the contribution from FAD from the contributions from all other fluorophors in the sample. Subsequent operation of the machine, on an unknown sample, would then yield results based only on the effects of FAD, and not on the other fluorophors in the sample. Thus, the present invention provides a reliable means of detecting fluorescence anisotropy from a particular fluorophor, even when the sample contains multiple fluorophors, and even when the contributions from the other fluorophors might otherwise mask the effect of the fluorophor of interest.

Moreover, a novel adaptation of the general methodology allows the preferred embodiment to provide greater sensitivity in non-invasively detecting and localizing disease-induced reductions in function and metabolic capacity within tissues. This may be accomplished in the human retina, in situ, by the following paradigm in which the retina is first imaged for orientation with 830 nm light, supplied by Laser 3 of FIG. 2, to which the retina is unresponsive, and then obtaining steady-state metabolic maps of the retina within 100 msec., which falls well within the latency of the metabolic response of the retina to saturating light. This procedure provides a steady-state fluorescence anisotropy map of the retina in the dark, resting state. Subsequently, the retina is imaged at 830 nm followed by 20-30 sec of flickered blue (488 nm) or green (514 nm) light supplied by the argon laser, Laser 1, at flicker rates ranging from 6-13 Hz and fluorescence anisotropy images acquired during flicker, thereby providing a measurement of the light, stimulated state of the retina. Dark and light fluorescence anisotropy maps can be aligned and subtracted pixel-by-pixel to yield a 2- or 3-dimensional map of the functional capacity of the retina to respond to light stimulation. In addition, by selection of different types of spatial, spectral or temporal configurations of light stimulation, one can isolate function and metabolism to different cell layers and types within the retina.

Although the preferred embodiment employs light stimulation in the case of the retina, it should be apparent that the same preferred embodiment might be applied to other bodily tissues by selecting some other mode of stimulation appropriate to the tissue being examined.

FIGS. 3A-3F illustrate the use of the present invention to detect changes in tissue metabolism. In the experiment represented by these figures, one eye of a monkey was subjected to slight damage by laser-induced occlusion of a large vein. The latter condition is known in the art as large branch vein occlusion (BRVO). FIGS. 3A-3F illustrate the ability of the present invention to detect this damage.

Figure 3D:
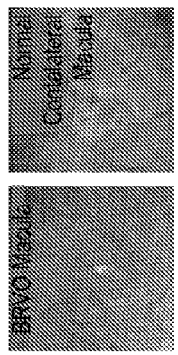
FIGS. 3A-3F provide diagrams illustrating the use of the present invention to detect changes in the condition of eye tissues in an animal by measurement of fluorescence anisotropy, where FIG. 3A provides a frequency histogram showing the variation of fluorescence anisotropy under different conditions, FIGS. 3B and 3C provide grayscale maps of fluorescence anisotropy values in the eye of an animal under different conditions, FIG. 3D provides infrared scans of treated and untreated eyes of an animal, and FIGS. 3E and 3F provide angiograms depicting the condition of the eye of an animal.
Figure 3E:
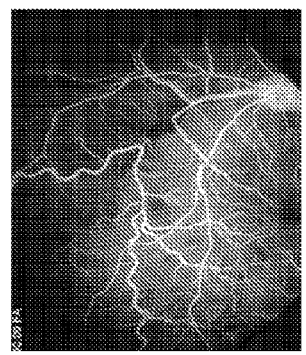
Figure 3F:
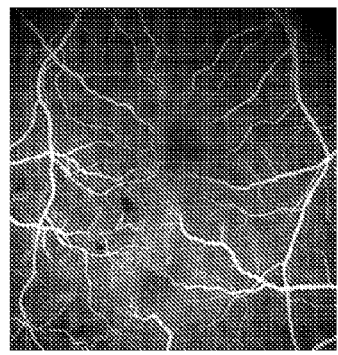
Figure 3A:
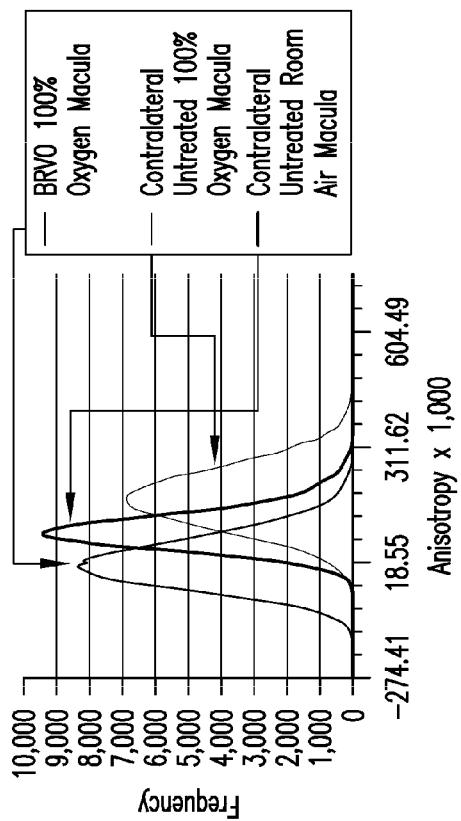

In the experiment represented by FIGS. 3A-3F, fluorescence anisotropy of the macula was measured under the following three conditions. First, fluorescence anisotropy of the macula of the damaged eye was measured, over a 20° visual field centered at the macula, while the animal was breathing pure oxygen. Secondly, fluorescence anisotropy of the macula of the undamaged ("contralateral") eye was measured, also while the animal was breathing pure oxygen. Thirdly, fluorescence anisotropy of the macula of the undamaged eye was measured while the animal was breathing room air. As shown in FIG. 3A, all three of these conditions yielded distinct graphs.

The normal, untreated eye shows increased fluorescence anisotropy values when the animal breathes pure oxygen as compared to room air. Also, the damaged eye provides significantly lower values of fluorescence anisotropy when the animal breathes pure oxygen, as compared to the untreated eye when the animal breathes room air. All comparisons were made with the same animal.

FIG. 3A therefore shows the use of the present invention in detecting subtle metabolic changes, insofar as the tissue metabolism is enhanced when the animal breathes pure oxygen, and is depressed by reducing blood flow to the tissue due to the induced vein occlusion. This induced damage would not have been detectable using conventional methods.

Figure 3C:
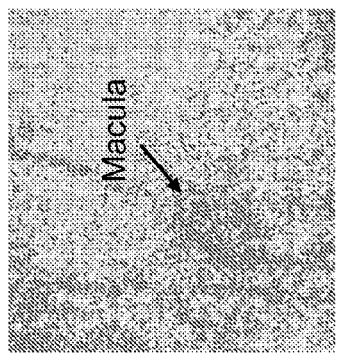
Figure 3B:
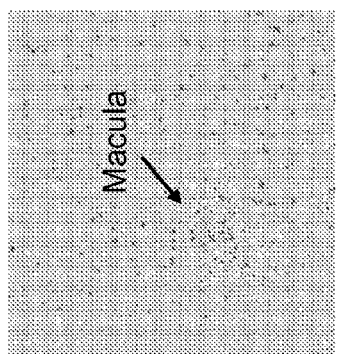

FIG. 3B provides a grayscale spatial map of fluorescence anisotropy values in the damaged eye, while the animal was breathing pure oxygen, over a 20° visual field. The dark areas correspond to high values and light areas to low values. FIG. 3C provides a similar map for the undamaged eye, also while the animal was breathing pure oxygen. Note that the fluorescence anisotropy values represented in FIG. 3B, while depressed across the entire 20° field as compared to FIG. 3C, show the most pronounced depression in the macula. Conversely, FIG. 3C shows increased anisotropy values across the entire field, as compared to FIG. 3B, with the most pronounced increase occurring at the macula.

FIG. 3D provides near-infrared scans, respectively, of the damaged and undamaged eye of the animal. FIG. 3E provides a fluorescein angiogram showing the site of the laser-induced branch vein occlusion. FIG. 3F provides a fluorescein angiogram of the damaged eye, centered at the macula, showing the tortuosity of vessels encroaching the macula.

The comparison of the curves in FIG. 3A can be performed visually, by a human operator, or the comparison could be automated, and performed by a programmed computer. In this regard, the computer shown in FIG. 2 should be considered a means for performing such comparison.

In grayscale metabolic maps, the dark areas correspond to high values and light areas to low values. The relationship between grayscale and quantitative values of fluorescence anisotropy is enhanced linearly to the same extent in images within the figure. Note that in this and all following figures, the frequency histograms are a plot of the frequency of occurrence of different fluorescence anisotropy values within the measurement area.

FIGS. 4A-4F illustrate the use of the present invention to identify disease. In particular, these figures illustrate the use of steady-state measurements of fluorescence anisotropy to identify diabetic retinopathy, in human retinal tissue in which the disease is accompanied by reduced metabolism of the retina. The invention is used to identify both moderate, non-proliferative diabetic retinopathy and mild proliferative diabetic retinopathy (PDR) in the temporal retina.

FIG. 4A provides a frequency histogram of fluorescence anisotropy values for a patient with moderate nonproliferative diabetic retinopathy, with the patient breathing room air. FIG. 4B provides a frequency histogram of fluorescence anisotropy values in normal, age and gender-matched control subjects, also breathing room air. Note that the mean of the histogram in FIG. 4A is shifted to lower values, and is wider, compared to the measurements taken for normal subjects, in FIG. 4B.

FIG. 4C provides a frequency histogram of fluorescence anisotropy values in the same patient represented in FIG. 4A, with the patient breathing pure oxygen. Note that the mean of anisotropy values for this patient is approximately equal to that of the control subject breathing room air (FIG. 4B).

FIG. 4D provides a frequency histogram of fluorescence anisotropy values of an age and gender-matched control subject breathing pure oxygen. Note that the histogram of FIG. 4C is wider than that of the control subject breathing pure oxygen (FIG. 4D).

FIG. 4E provides a graph showing normalized mean values of patients with mild PDR compared to normal age- and gender-matched controls (n=20) error bars are +/−1 S.E.M. The bars labeled with asterisks indicate that the results had statistical significance at the P value shown. The middle bar represents a test on a single patient, too small of a sample for statistical significance. Nevertheless, the mean fluorescence anisotropy value of that patient, who had diabetes for about ten years, without overt retinopathy, shows intermediate depression of fluorescence anisotropy values, relative to the first and third bars, as demonstrated by fluorescein angiography.

FIG. 4F provides a near infrared scan of a retina, showing the area of interest in the temporal retina from which fluorescence anisotropy frequency histograms were generated.

As before, the computer shown in FIG. 2 can be considered a means for performing the comparisons among the curves shown in FIGS. 4A-4D, and/or among the bars in FIG. 4E.

FIGS. 5A-5H illustrate the use of the present invention in detecting and localizing functional and metabolic deficits in tissues by quantitatively subtracting the fluorescence anisotropy maps of a tissue in the resting state from those obtained in the same tissue in a stimulated state. The invention thereby allows quantitative determination and localization of regions within the tissue that show reduced capacity to respond to stimulation.

FIG. 5A provides a metabolic map of a 20° field, centered at the optic disc of the retina, showing fluorescence anisotropy in space, in the dark, resting state. Note that, in the dark, the temporal retinal and temporal neuroretinal rim are depressed relative to the nasal retina and neuroretinal rim.

FIG. 5B provides a metabolic map of the same region as FIG. 5A, after 20 seconds of flickered light stimulation at 12 Hz. Note that flickered light causes fluorescence anisotropy values to increase across the entire field relative to FIG. 5A.

FIG. 5C shows the result when the images of FIGS. 5A and 5B were aligned, and one image was subtracted from the other, pixel-by-pixel, to yield a functional map of the 20° visual field (b-a) in response to flickered light stimulation. Note that the temporal retina and temporal neuroretinal rim become dominant. The relationship between grayscale and quantitative values of fluorescence is enhanced linearly to the same extent in all images within the figure and the lighter regions correspond to high values and the darker to low.

FIG. 5D provides an infrared scan of the same region shown in FIGS. 5A-5C, for orientation.

FIG. 5E provides a graph showing the vertical average between the horizontal lines in FIG. 5A (darkness) as a function of distance in pixels. The smooth curve is a 20th order Chebyshev polynomial fit ($r^2$=0.9818). The values are plotted from the temporal to nasal sides. The residuals were normally distributed.

FIG. 5F provides a graph of the vertical average between the horizontal lines in FIG. 5B (after flickered light) as a function of distance in pixels. The smooth curve is a 20th order Chebyshev polynomial fit ($r^2$=0.7806). The values are plotted from the temporal to nasal sides. The residuals were normally distributed.

FIGS. 5G and 5H provide frequency histograms of fluorescence anisotropy values for the 20° field and disc, respectively, in darkness and after flickered light.

The computer and monitor shown in FIG. 2 can be used as means for performing the above analyses. The patterns shown in FIGS. 5A-5D can be displayed on the monitor, while the calculations needed to form the difference image of FIG. 5C can be performed by the computer. The computer may also be used to generate the fitted curves of FIGS. 5E and 5F, and to generate and compare the curves shown in FIGS. 5G and 5H.

FIGS. 6A-6G illustrate the use of the present invention to identify disease states non-invasively in humans. In this example, the disease is primary open angle glaucoma (POAG).

Figure 6A:
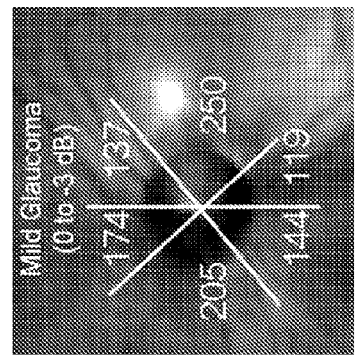
FIGS. 6A-6G illustrate the use of the present invention in detecting glaucoma, where FIG. 6A-6B provide grayscale maps of fluorescence anisotropy values in patients with and without glaucoma, FIG. 6C provides a graph of anisotropy values for various patients, FIGS. 6D-6E provide diagrams showing fluorescence anisotropy values for patients with and without glaucoma, and FIGS. 6F-6G provide diagrams showing corresponding results, for the same patients, using conventional diagnostic techniques.
Figure 6B:
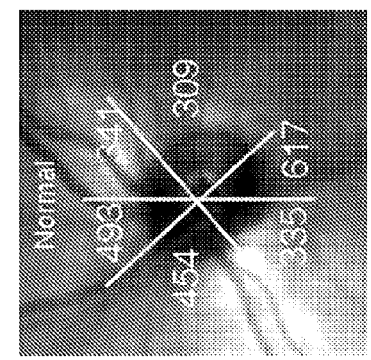

FIG. 6A provides a grayscale map of steady-state fluorescence anisotropy values in a 20° field, centered at the optic disk, in a retina of a normal (control) patient. FIG. 6B provides a similar map for a patient with mild POAG.

Figure 6C:
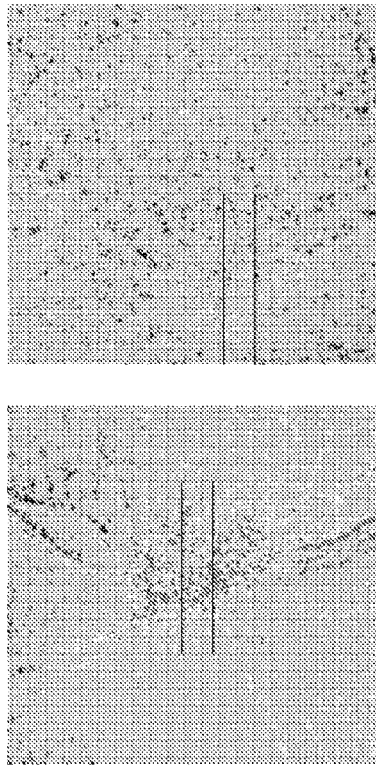

FIG. 6C provides graphs of fluorescence anisotropy values, across the optic disk, for a normal patient, a patient with mild POAG, and a patient with severe POAG. Thus, the present invention is capable of not only identifying the presence of the disease, but also of distinguishing among degrees of its severity.

Figure 6D:
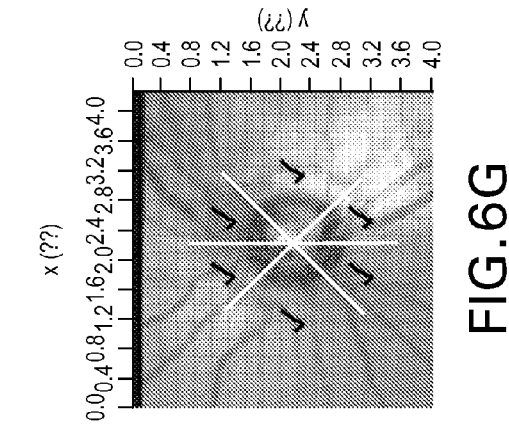
Figure 6E:
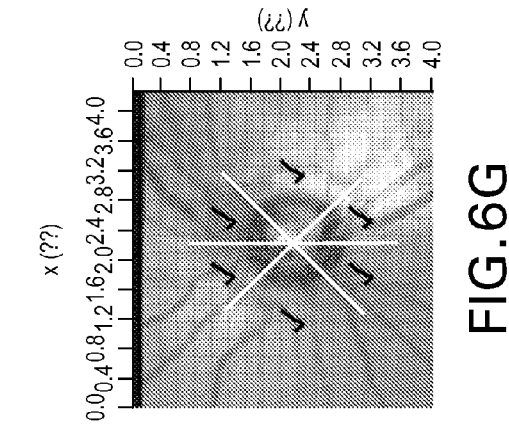

FIGS. 6D and 6E provide diagrams showing fluorescence anisotropy values measured at different areas of the neuroretinal rim of a normal control (FIG. 6D) and a patient with mild POAG (FIG. 6E). Note that the values of the patient with mild disease are depressed at all loci.

Figure 6F:
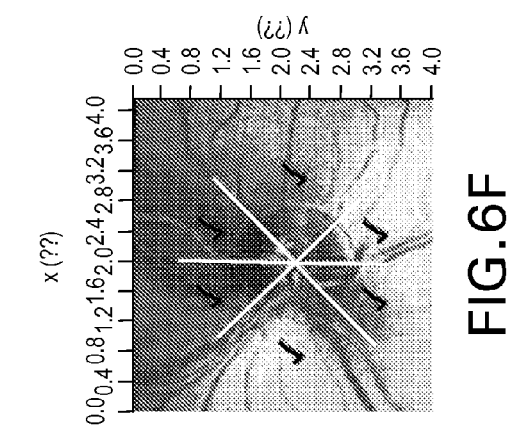
Figure 6G:
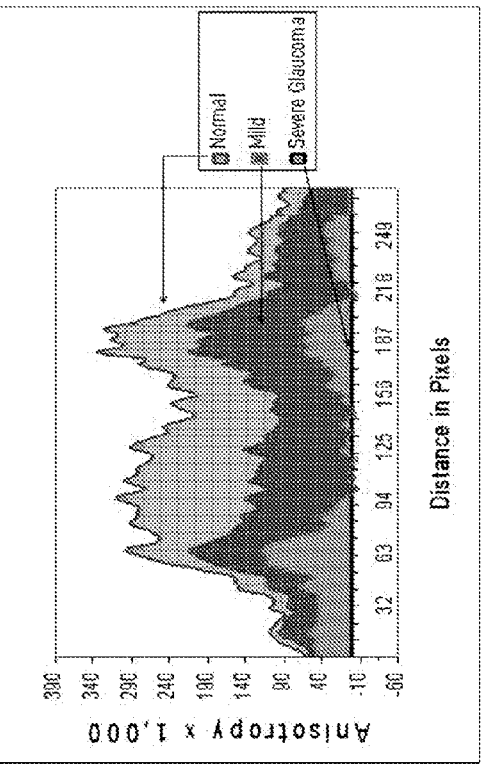

FIGS. 6F and 6G illustrate measurements made with the Heidelberg HRTII, the device most commonly used to detect glaucoma, for the normal patient, and the patient with mild disease, of FIGS. 6A and 6B, respectively. Thus, the prior art device fails to distinguish between the normal control and the patient with mild disease.

The computer, shown in FIG. 2, can therefore be programmed to generate and analyze curves such as those shown in FIG. 6C, and to produce diagnoses, indicating whether a disease state exists, and the extent of its severity.

FIGS. 7A-7F illustrate the use of the present invention to detect subtle changes in blood flow and reduced function and metabolism of tissues of the eye, by measuring steady-state fluorescence anisotropy. In particular, these figures, taken from observations of the eyes of a monkey, illustrate the use of the present invention in detecting ocular hypertension (OHT). The present invention detects subtle effects which are not always observable by use of optical coherence tomography, which is the most sensitive known method of the prior art.

FIG. 7A provides frequency histograms of fluorescence anisotropy values for 20° visual fields centered at the optic disks of a normal, untreated eye and an eye having OHT, of the same monkey, under conditions where the monkey was breathing pure oxygen. The values of fluorescence anisotropy for the diseased eye are lower than the values for the healthy eye. FIG. 7B shows a normal, untreated optic disk, using ocular coherence tomography (OCT), and FIG. 7C shows an optic disk having OHT, again using the technique of OCT. The lowered values of fluorescence anisotropy for the diseased eye correspond to the excavation of the disk shown in FIG. 7C.

FIG. 7D provides frequency histograms of fluorescence anisotropy values of 20° visual fields centered at the macula, for a normal untreated eye, and an OHT eye, under conditions where the animal was breathing pure oxygen. Note the marked depression of fluorescence anisotropy values for the ocular hypertensive macula as compared to macula of the normal eye. This pronounced depression of fluorescence anisotropy values with increased intraocular pressure is present despite the fact that no evidence of structural damage is revealed by OCT. FIGS. 7E and 7F provide tomographs of a normal and diseased eye, respectively, of the same monkey. All of the OCT maps were of very high quality due to the monkey being paralyzed, thereby removing motion artifacts normally associated with OCT measurements. All data in FIGS. 7A-7F came from the same animal. Comparison of the curves shown in FIGS. 7A and 7D can be performed by the computer shown in FIG. 2.

Figures 8A, 8B:
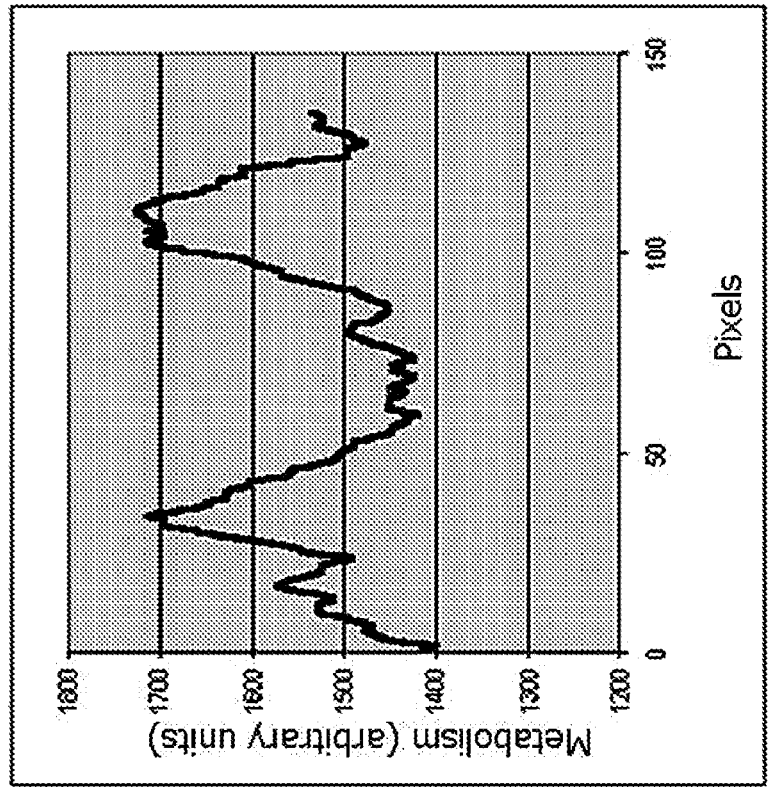
FIGS. 8A and 8B illustrate the use of the present invention to evaluate the effectiveness of treatment for diabetic retinopathy, where FIG. 8A provides a two-dimensional map of fluorescence anisotropy of a region of the retina, showing treated and untreated areas, and FIG. 8B provides a graph showing fluorescence anisotropy values measured along the line drawn in FIG. 8A.

FIGS. 8A-8B illustrate the use of the present invention to reveal the efficacy of treatment interventions, through measurement of steady-state fluorescence anisotropy. In this case, panretinal photocoagulation was used to treat proliferative diabetic retinopathy.

FIG. 8A depicts a fluorescence anisotropy 2-dimensional map of a region in the peripheral retina of a diabetic patient with proliferative disease, showing untreated tissue and two laser photocoagulated small regions. A computer-drawn line for analysis is placed across the region showing untreated and treated areas. FIG. 8B provides a graph showing steady-state fluorescence anisotropy values, measured along the line profile. As explained above, tissue metabolism is correlated with fluorescence anisotropy. The graph shows that tissue metabolism is increased by laser treatment, thereby providing an indication of the efficacy of the treatment.

While the examples given above deal with disease states within the human retina, it should be apparent to one skilled in the art that the methodology of the present invention may be used to detect changes that fall within two general classes of biologic change, namely angiogenesis and apoptosis.

Angiogenesis is the process of development of new blood vessels to meet the metabolic requirements of the tissue, which in normal development follows a coordinated course leading to the formation of competent blood vessels that follow a pattern governed by the changes in metabolism that occur during development. However, numerous disease states involve aberrant metabolism that leads to the uncoordinated florid growth of new blood vessels that may be leaky or incompetent.

One notable class of diseases to which the methodology of the present invention may be applied is in cancers that develop and can have potentially lethal consequences. The sequence of events that is generally accepted in the field of angiogenesis is that tissue hypoxia, low levels of tissue oxygenation, resulting from increased metabolism or reduced blood flow, in turn cause upregulation of genes that express vascular endothelial growth factor (VEGF). VEGF has, in addition to other angiogenic growth factors, been demonstrated to cause new blood vessel growth. The example of diabetic retinopathy, described above, illustrates one such case. In cancers of numerous origin and tissue involvement, tumors show increased metabolism that may be detected by the present invention before they may be identified visually. Tumors can only grow in size if new blood vessels develop to nourish the tumor and structural technologies employing contrast agents in CT scanning and MRI scanning look for enhancement of the visualized mass upon injection of contrast agents that flow through the newly formed blood vessels. The present invention allows the detection of increased metabolism prior to new blood vessel growth, allowing tumors to be ablated at their earliest stages, thereby reducing the need for extensive chemotherapeutic and radiation interventions.

Wound healing presents another interesting application of the methodology of the present invention. A key question in surgical removal of dead tissue is the distinction between living and dead (metabolically inactive tissue). Similarly new blood vessels need to grow to support the joining of two living tissues. The present invention can be used to distinguish between living and dead tissue and tissue capable of sustaining coordinated blood vessel growth.

It should be apparent to one skilled in the art that the above is not an exhaustive list of diseases to which the methodology may be applied. For example, there are a host of mitochondrial diseases that are genetically passed from generation to generation. Such mitochondrial diseases may be detected and imaged using the techniques of the present invention, based upon the aberrant metabolic consequences of these diseases.

Apoptosis is an orchestrated form of cell death that proceeds normally in the continuing renewal of tissues within the body. However, disease states may, as in the case of angiogenesis, cause the process to become uncoordinated, with severe consequences to patients. The present invention provides one example of apoptosis that proceeds in an aggressive manner, in the cases of glaucoma and other optic neuropathies.

Glaucoma belongs to a large family of neurodegenerative diseases that include Huntington's, Parkinson's and Alzheimer's diseases. The methods of the present invention may be applied to detect other diseases of this type at early stages.

For example, Alzheimer's disease is associated with destruction of retinal nerve fibers and ganglion cells. However, structural imaging in Alzheimer's disease only reveals the disease in the retina at relatively advanced stages when cells have died. It is well known that metabolic dysfunction precedes apoptosis in all tissues and the methodology herein disclosed may allow the detection of Alzheimer's and other neurodegenerative diseases at their earliest stages during a routine eye exam.

One interesting case in which the physician intentionally induces apoptosis, cell death, is in the area of cancer treatment by means of chemotherapeutic agents and/or radiation. Just as cellular dysfunction and reduced metabolism precede apoptosis, energy is required to initiate the final step of apoptosis, causing the cells to die and pass the point of no return. This burst of metabolism may be visualized using steady-state flavoprotein fluorescence anisotropy imaging, thereby allowing the oncologist to provide sufficient chemotherapeutic agents to kill cancerous cells while halting or reducing the dose of such agents to avoid the dire side effects of chemo- and radiation-therapies.

An exceedingly important application of the methodology of the present invention is in the field of anesthesiology. The goal of the anesthesiologist, during all procedures, is to protect the brain from irreversible damage. Indeed, cognitive losses have been reported in long surgeries such as bypass surgery and carotid endarterectomies, to name two. The retina, in addition to being a part of the brain, is the most metabolically active part of the brain. Currently, all that may be measured is the partial pressure of oxygen in the blood while it is brain tissue oxygenation and metabolic rate that is critical to protecting the brain from irreversible damage. By imaging the retina with the technology of the present invention, during surgeries, it will be possible to measure reduced tissue metabolism in the retina that precedes dysfunction and cell death within the rest of the brain, and thereby to adjust oxygen supply to the patient to avoid irreversible brain damage. Just as too little oxygen can be damaging so may supplying too much oxygen for prolonged periods of time and that is why the methodology of the present invention may, when compared to a database of normal metabolic levels, be used to adjust oxygen delivery to the patient to provide appropriate and protective levels of oxygen. The comparison and use of a database for all disease states and determination of normal values will permit threshold values for normal metabolism to be determined and allow treatment modalities to be employed to restore regions of tissue metabolism to their normal levels. Such databases can be determined in clinical trials.

The present specification has focused thus far on one of the substrates of metabolism, namely oxygen. Glucose is, of course, the second major substrate in the pathway of oxidative metabolism. Numerous methodologies have been proposed, and some implemented, for the measurement of blood glucose. However, just like oxygen, it is the level of glucose supplied to the mitochondria of living cells within tissues that is most important. The methods of the present invention provide a unique opportunity to measure mitochondrial metabolism and glucose supply when the second substrate—oxygen—is held constant. Indeed, in humans with diabetes, the oxygen level supplied to the patient in everyday life is the percentage of oxygen in room air, which remains constant. Therefore the present invention provides an entirely different means of titrating glucose and insulin in diabetic patients while achieving the goal of doing so by a noninvasive method. Handheld devices used in the home healthcare field may be developed that monitor mitochondrial function and its change by blood glucose, insulin or oral diabetic drugs that may be performed by flashes of polarized light to the eye. Unlike numerous other approaches that center on blood glucose where the signal-to-noise level levels may be low, the present methodology achieves high signal-to-noise levels as demonstrated in the examples herein provided.

Since mitochondrial metabolism is essential to life, it will be apparent to those skilled in the art that the methodology described herein may have far-reaching applications to multiple medical disciplines.

Similarly, the implementations of the methods presented in the schematics of FIGS. 1 and 2 are but two of many that may be devised based upon the present method. Steady-state flavoprotein fluorescence anisotropy imaging may be applied to any tissue that may be imaged directly—the eye, skin, cervix etc.—and may easily be incorporated into endoscopic devices used to examine internal organs such as the esophagus, stomach, gut or lungs, or laparoscopic and arthroscopic devices that are currently in use in medicine. In addition, miniaturized catheters that may be inserted into blood vessels and other small caliber regions may be fabricated employing the method of the present invention, by means of the use of single mode polarization preserving optical fibers.

The invention can be modified in other ways which will be apparent to those skilled in the art. The specific arrangements shown in FIGS. 1 and 2 can be varied considerably, and there are many ways to implement the methods described above. Such modifications should be considered within the spirit and scope of the following claims.

What is claimed is:
1. A non-destructive method of evaluating the functional capacity of a living human tissue in situ in an intact living human being, comprising:
  (a) non-destructively imaging a first resting steady-state fluorescence anisotropy map of said tissue within a latency period of metabolic change in response to a stimulus that changes metabolism and function by the following steps:
  (i) irradiating the tissue with continuous linearly polarized light sufficient to cause endogenous lipoamide dehydrogenase (LipDH) to fluoresce within the latency period of metabolic change to light, and capturing the fluorescence emission prior to the excitation light causing the tissue to change its metabolism;
  (ii) resolving the emitted fluorescence from said LipDH into vector components parallel and perpendicular to the plane of the exciting polarized light;
  (iii) calculating the steady-state fluorescence anisotropy (A) of said LipDH from the resolved vector components; and
  (iv) constructing a steady-state fluorescence anisotropy map image of said tissue;

(b) non-destructively imaging a second stimulated steady-state fluorescence anisotropy map of said tissue for a second metabolic or functional state by the following steps:
  (i) irradiating the tissue with continuous linearly polarized light sufficient to cause endogenous LipDH to fluoresce after the latency period of metabolic change to light, and capturing the fluorescence emission after the stimulus has caused the tissue to change its metabolism; and
  (ii) repeating parts (ii), (iii) and (iv) of step (a);
(c) determining the functional capacity of the tissue by subtracting point by point or pixel by pixel the first resting steady-state fluorescence anisotropy image from the second stimulated steady-state fluorescence anisotropy image, over the entire imaged field or within areas of interest; and
(d) comparing the functional capacity of the tissue under evaluation to a database of normal metabolic levels obtained from control tissue similarly determined by steps a-c to reveal dysfunctional areas in the tissue under evaluation.

2. The method of claim 1, wherein said first and second maps comprise two dimensional steady-state fluorescence anisotropy images.

3. The method of claim 2, wherein said two dimensional steady-state fluorescence anisotropy images are obtained at a plurality of depths within the tissue.

4. The method of claim 1, wherein three-dimensional volume maps are constructed for both the tissue subject to evaluation and the control tissue.

5. The method of claim 4, wherein metabolic and functional deficits are revealed in three dimensional space.

6. The method of claim 1, wherein said stimulus includes light stimulation and stimulation by means other than light.

7. The method of claim 5, wherein deficits resulting from disease or effects of a therapeutic or surgical treatment are localized in three dimensional space when compared to three dimensional volumes of functional capacity determined in normal untreated control subjects.

8. The method of claim 1, wherein said tissue subjected to evaluation comprises ocular tissue.

9. The method of claim 6, wherein the stimulus is light.

10. The method of claim 1, wherein said LipDH fluorophor emission is isolated from metabolically inert fluorophor emissions based on their respective steady-state fluorescence anisotropy values.

11. The method of claim 1, wherein said LipDH is in direct equilibrium with the $NAD^+/NADH$ pool in the mitochondria.

12. The method of claim 1, wherein the stimulus causes both the tissue subject to evaluation and the corresponding control tissue to change their respective steady-state fluorescence anisotropies (A) due to changes in the rotational correlation time ($\phi$) of any segment of LipDH free to rotate by a magnitude that exceeds the stimulus induced changes in the fluorescence lifetimes ($\tau$) of both tissues according to the following equation:

$$\frac{A_o}{A} = 1 + \frac{\tau}{\phi} = 1 + \sigma$$

where $A_0$ is a limiting value in the absence of rotation given by the relative orientation of the absorption and emission dipole transition moments of LipDH and $\sigma$ is the ratio of $\tau/\phi$.

* * * * *